United States Patent
Tsukamoto

(10) Patent No.: US 10,428,138 B2
(45) Date of Patent: Oct. 1, 2019

(54) ANTIBODY AND ANTIBODY-CONTAINING COMPOSITION

(71) Applicants: Ostrich Pharma KK, Kyoto (JP);
Immortal Spirit Limited, Hong Kong (HK)

(72) Inventor: Yasuhiro Tsukamoto, Osaka (JP)

(73) Assignees: Ostrich Pharma KK, Kyoto (JP);
Immortal Spirit Limited, Hong Kong (HK)

( * ) Notice: Subject to any disclaimer, the term of this patent is extended or adjusted under 35 U.S.C. 154(b) by 0 days.

(21) Appl. No.: 16/133,493

(22) Filed: Sep. 17, 2018

(65) Prior Publication Data

US 2019/0016788 A1  Jan. 17, 2019

Related U.S. Application Data

(60) Continuation of application No. 15/808,807, filed on Nov. 9, 2017, now Pat. No. 10,106,599, which is a
(Continued)

(30) Foreign Application Priority Data

Aug. 19, 2011 (JP) .................................. 2011-179378

(51) Int. Cl.
*A61K 39/00* (2006.01)
*C07K 16/02* (2006.01)
(Continued)

(52) U.S. Cl.
CPC ........ *C07K 16/1271* (2013.01); *C07K 16/084* (2013.01); *C07K 16/085* (2013.01);
(Continued)

(58) Field of Classification Search
None
See application file for complete search history.

(56) References Cited

U.S. PATENT DOCUMENTS 6,162,441 A  12/2000  Chae et al.
6,849,419 B1  2/2005  Wakasugi et al.
(Continued)

FOREIGN PATENT DOCUMENTS

CN  1362418  8/2002
CN  1454901  11/2003
(Continued)

OTHER PUBLICATIONS

Adachi et al., "Development of neutralization antibodies against highly pathogenic H5N1 avian influenza virus using ostrich (*Struthio camelus*) yolk," Mod Med Rep (2008) 1(2):203-209.
(Continued)

*Primary Examiner* — Michelle S Horning
(74) *Attorney, Agent, or Firm* — Morrison & Foerster LLP

(57) ABSTRACT

For many diseases due to microbes or the like, proliferation of microbes themselves is a cause of a symptom. However, there were cases where a substance released by the microbes is a cause of a symptom. In such cases, when attempting to treat a disease with an antibody, it was necessary to obtain an antibody against an antigen that is a substance causing the disease. However, it was difficult to find the underlying substance causing the disease among substancesa released by the microbes. An antibody (polyclonal) binding to not only an antigen but also to a substance, which is secreted by the antigen and accelerates the deterioration of a symptom, is obtained by immunizing birds with a lysis solution produced from lysing microbial cells as an antigen. Further,
(Continued)

an antibody obtained with a surface protein of a virus as an antigen is expected to inhibit an infection by a virus.

5 Claims, 2 Drawing Sheets

Related U.S. Application Data continuation of application No. 15/230,188, filed on Aug. 5, 2016, now Pat. No. 9,828,419, which is a division of application No. 14/239,776, filed as application No. PCT/JP2012/005056 on Aug. 9, 2012, now abandoned.

(51) Int. Cl.
  *C07K 16/12* (2006.01)
  *C07K 16/08* (2006.01)
  *C07K 16/10* (2006.01)

(52) U.S. Cl.
  CPC ...... *C07K 16/1045* (2013.01); *C07K 16/1063* (2013.01); *C07K 16/1267* (2013.01); *C07K 2317/11* (2013.01); *C07K 2317/23* (2013.01); *C07K 2317/76* (2013.01); *C12N 2710/14043* (2013.01)

(56) References Cited

U.S. PATENT DOCUMENTS

| | | | |
|---|---|---|---|
| 6,919,080 | B2 | 7/2005 | Tokunaga et al. |
| 7,005,503 | B2 * | 2/2006 | Hua .................. C07K 16/2866 424/133.1 |
| 8,765,133 | B2 | 7/2014 | Tsukamoto |
| 8,815,244 | B2 | 8/2014 | Tsukamoto |
| 9,828,419 | B2 | 11/2017 | Tsukamoto |
| 2003/0027987 | A1 | 2/2003 | Tokunaga et al. |
| 2004/0096447 | A1 | 5/2004 | Yasuda et al. |

FOREIGN PATENT DOCUMENTS

| | | |
|---|---|---|
| CN | 1569896 | 1/2005 |
| CN | 1680445 | 10/2005 |
| CN | 1253198 | 8/2008 |
| EP | 1 930 346 | 6/2008 |
| JP | 2-121910 | 5/1990 |
| JP | H02 121910 | 5/1990 |
| JP | 10-84969 | 4/1998 |
| JP | 2002-122594 | 4/2002 |
| JP | 2002-212100 | 7/2002 |
| JP | 2002-326958 | 11/2002 |
| JP | 2003-503015 | 1/2003 |
| JP | 2005-537028 | 12/2005 |
| JP | 2007-084495 | 4/2007 |
| JP | 2008-169142 | 7/2008 |
| JP | 2009-023985 | 2/2009 |
| JP | 2010-013361 | 1/2010 |
| JP | 2011-105614 | 6/2011 |
| KR | 2000-0048855 | 7/2000 |
| KR | 10-2010-0111791 | 10/2010 |
| WO | WO-98/14209 | 4/1998 |
| WO | WO-02/083737 | 10/2002 |
| WO | WO-03/104280 | 12/2003 |
| WO | WO-2004/002416 | 1/2004 |
| WO | WO-2007/026689 | 3/2007 |

OTHER PUBLICATIONS

Database WPI, accession No. 2004-043641 (Dec. 2003), 4 pages.
Day et al., "Mechanisms of Human Papillomavirus Type 16 Neutralization by L2 Cross-Neutralizing and L1 Type-Specific Antibodies," J Virol (2008) 82(9):4638-4646.
Inoue, "Protection against uterine cervical cancer by HPV vaccines," Virus (2008) 58(2):155-164.
Japan Science and Technology Agency," JST Highlights," (2010) pp. 1-41 Retrieved from the Internet: URL: http://www.jst.go.jp/EN/highlights2010.pdf. Retrieved on Jun. 14, 2016.
Kennedy et al., "Targeting of Alpha-Hemolysin by Active or Passive Immunization Decreases Severity of USA300 Skin Infection in a Mouse Model," Journal of Infectious Diseases (2010) 202(7):1050-1058.
Nakata et al., "A high incidence of *Staphylococcus aureus* colonization in the external eyes of patients with atopic dermatitis," Ophthalmology (2000) 107(12):2167-71.
Shin et al., "Use of Egg Yolk-Derived Immunoglobulin as an Alternative to Antibiotic Treatment for Control of Helicobacter pylori Infection," Clinical and Diagnostic Laboratory Immunology (2002) 9(5):1061-1066.
Villa et al., "Immunologic responses following administration of a vaccine targeting human papillomavirus Types 6, 11, 16 and 18," Vaccines (2006) 24:5571-5583.

* cited by examiner

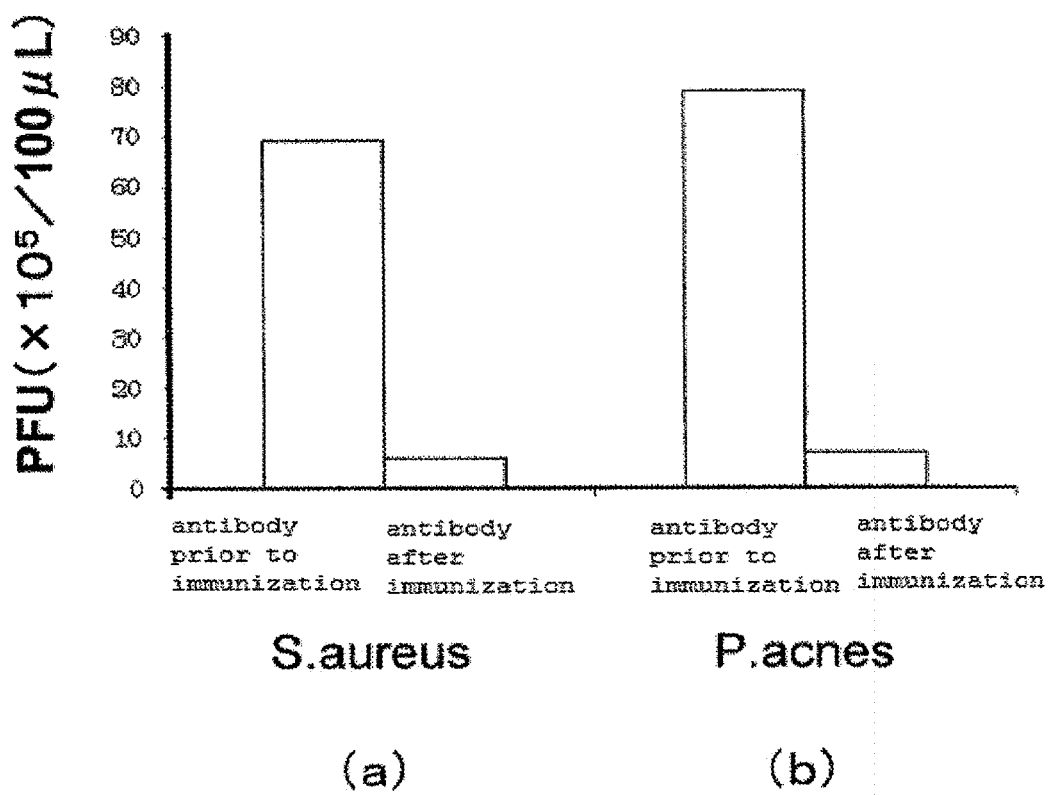

[Figure 2]
(a)          (b)

ANTIBODY AND ANTIBODY-CONTAINING COMPOSITION

CROSS-REFERENCE TO RELATED APPLICATIONS

This application is a continuation of U.S. patent application Ser. No. 15/808,807, filed Nov. 9, 2017, now U.S. Pat. No. 10,106,599, which is a continuation of U.S. patent application Ser. No. 15/230,188, filed Aug. 5, 2016, now U.S. Pat. No. 9,828,419, which is a divisional of U.S. patent application Ser. No. 14/239,776, filed May 9, 2014, now abandoned, which is the U.S. National Stage of International Application Number PCT/JP2012/005056 filed Aug. 9, 2012, which claims priority to Japanese Patent Application Number 2011-179378 filed Aug. 19, 2011. The contents of the above applications are incorporated herein by reference in their entireties for all purposes.

TECHNICAL FIELD

The present invention relates to an antibody against a microbial cell as an antigen, and an antibody-containing composition consisting of the antibody and a base. The present invention also relates to an antibody against a surface protein of a virus as an antigen, and an antibody-containing composition consisting of the antibody and a base.

BACKGROUND ART

Since an antibody selectively binds to an antigen, antibodies are applied in a variety of fields. For example, an assay targeting an antigen and use in a vaccine for inactivating an antigen are known. Further, application in filters is also known, where a filter captures an allergen substance that is constantly suspended in an atmosphere, such as microbes, fungus, or pollen.

Patent Document 1 discloses an invention of a filter carrying an antibody for capturing such harmful substances and a silver salt of an organic compound. Patent Document 1 discloses not only that microbes or the like are captured and are inactivated, but also that fungus and microbes do not newly proliferate on the carrier.

Patent Document 1: Japanese Laid-Open Publication No. 2009-233557

SUMMARY OF INVENTION

Problems to be Solved by the Invention

Several methods for obtaining antibodies are known. For example, the following method is known: immunizing a mouse with an antigen, fusing an antibody producing cell obtained from the mouse with an immortalized cell to form a hybridoma, and then culturing the hybridoma to obtain an antibody (monoclonal).

Further, a method of immunizing an oviparous animal including birds to obtain an antibody from their eggs is known. However, it was merely possible to obtain only an antibody against a target antigen in the past.

Meanwhile, for many diseases due to microbes or the like, although proliferation of microbes themselves is a cause of a symptom, a substance released by the microbes can also be a cause of a symptom. In such cases, when attempting to treat a disease with an antibody, it was necessary to obtain an antibody against an antigen that is the substance causing the disease. However, it was difficult to find the underlying substance causing the disease among substances released by the microbes.

Further, although various antibiotics and sterilizing agents have been developed recently for use in skin disease, much of the indigenous bacteria is sterilized or eliminated by such an antibiotic or sterilizing agent. Thus, these were known to cause deterioration in microbial environment of the skin to exacerbate the skin disease. For this reason, it is necessary to inhibit only pathogens among the indigenous microbiota. However, a material with such selectivity has yet to be developed in a practical application.

An antibody is a protein with a property of specific binding to an antigen. Thus, it was conceived that an antibody can selectively bind only to a specific pathogen among numerous microorganisms present on the body surface or in the body to inhibit proliferation of, or kill the specific pathogen. That is, if only adverse microbes can be attacked with an antibody but not the indigenous bacteria (beneficial bacteria) protecting the skin, alleviation of a lesion or symptom can be expected as a result.

Along a similar reasoning, for adverse viruses for a human body that infect through the skin or mucous membrane, a reduction in infection can be expected by an antibody binding to such viruses at the body surface prior to entering the body.

Means for Solving the Problem

The present invention was conceived in view of the problem as described above. The present invention has been achieved by discovering that an antibody (polyclonal) binding to not only an antigen but also to a substance, which is secreted by a microbial cell used as an antigen and accelerates the deterioration of a symptom, is obtained by immunizing birds with a lysis solution produced by lysing microbial cells as an antigen. More specifically, an antibody of the present invention is an antibody against a lysis solution of microbial cells as an antigen.

Further, the present invention has been achieved by discovering that an antibody, which binds to a surface of a virus, can be obtained by immunizing birds with a protein on the surface of the virus as an antigen. More specifically, an antibody of the present invention is an antibody against a surface protein of a virus as an antigen.

Further, an antibody-containing composition comprising such an antibody and a base can attain the effect of the antibody by direct application on the skin.

Advantageous Effects of Invention

With regard to an antibody of the present invention, it is possible to obtain an antibody that binds to a microbial cell and to a substance which causes progression of a symptom from the microbial cell, despite immunizing only with the microbial cell. Thus, there is no need to obtain an antibody by using various substances as an antigen.

Further, an antibody of the present invention is an antibody against a surface protein of a virus as an antigen. Thus, the antibody can bind to the surface of a virus and reduce infections to a human body.

Further, it was found that an antibody-containing composition using an antibody of the present invention and a base has an effect of alleviating atopy or acne by direct application to the skin.

BRIEF DESCRIPTION OF THE DRAWINGS

FIG. 1 is a graph showing an experimental result demonstrating the effect of an antibody of the present invention in inhibiting proliferation of bacteria.

FIG. 2 is a picture demonstrating the effect of an antibody of the present invention in inhibiting proliferation of bacteria.

EMBODIMENTS FOR CARRYING OUT THE INVENTION

Specific Examples of the present invention will be shown below.

EXAMPLE 1

Bacteria

The two types of bacteria subjected to an Example demonstrating the effect of the present invention are *Staphylococcus aureus* (NBRC 102135) (hereinafter, referred to as *S. aureus*) and *Propionibacterium acnes* (NBRC 107605) (hereinafter, referred to as *P. acnes*).

Each of the culture suspensions of the bacteria described above were centrifuged and precipitated. The culture solution was removed, a phosphate buffer solution was added to resuspend the bacteria, and the bacterial cells were lysed by a homogenizer. An ostrich was immunized with said lysis solution (homogenate) as an antigen.

Immunization of Ostrich

100 µg each, in terms of protein abundance, of homogenates described above was mixed with a Freund's complete adjuvant and the mixture was inoculated in the muscle at the lumbar region of a female ostrich as a prime immunization. Thereafter, the two types of homogenates described above were both administered three times every other week as a booster immunization after the prime immunization. Also for such booster immunizations, 100 µg of bacterial homogenate solution was mixed with a Freund's incomplete adjuvant, and the mixture was inoculated into the muscle at the lumbar region of the female ostrich, which had already been immunized.

Purification of Antibody

An antibody was purified from an ostrich egg laid two weeks or more after the booster immunization. A method of purifying an antibody is shown below. Purification of an antibody (IgY) from a yolk was performed as follows.

First, TBS (20 mM Tris-HCl, 0.15 M NaCl, and 0.5% $NaN_3$) at five times the amount of a yolk and the same amount of 10% dextran sulfate/TBS are added to the yolk and the mixture is stirred for 20 minutes. In addition, 1M $CaCl_2$/TBS in an amount same as the yolk is added, and the mixture is stirred and is incubated for 12 hours. Thereafter, the mixture is centrifuged at 15000 rpm for 20 minutes and supernatants are collected. Next, ammonium sulfate is added so that the final concentration is 40% and the mixture is incubated at 4° C. for 12 hours. Thereafter, the mixture is centrifuged at 15000 rpm for 20 minutes and precipitates are collected. Finally, it is resuspended in the same amount of TBS as the yolk, and dialyzed with TBS. Collection of IgY with a purity of 90% or more was enabled by such a process. 2-4 g of IgY was able to be purified from one yolk.

Measurement by ELISA

Antibody reactivity of the obtained antibody was measured by the following ELISA. 100 µl of each of 2 µg/mL bacterial cells (*S. aureus* or *P. acnes*), enterotoxins of *S. aureus*, TSST-1 of *S. aureus*, coagulase, and protease was placed in each well of a 96-well microplate for ELISA and was incubated at room temperature for two hours. After washing three times with PBS, 100 µl of a commercially available blocking solution (Block Ace: Dainippon Sumitomo Pharma Co., Ltd.) was placed in each well and the mixture was incubated for two hours. After washing three times with PBS, 50 µl of a serial dilution solution (with 2 mg/mL as the stock solution, a two-fold serial dilution such as 100 times, 200 times etc.) of an ostrich IgY antibody prior to and after immunization was placed in each well and was incubated at room temperature for one hour.

After washing three times with PBS, 100 µl of peroxidase labeled anti-ostrich IgY rabbit polyclonal antibody (self-produced) was placed in each well and incubated for 45 minutes. After washing three times with PBS, a commercially available luminescence kit for peroxidase (Sumitomo Bakelite Co., Ltd) was used and 30 minutes after the emission of luminescence, the absorbance (450 nm) was measured by a plate reader for ELISA. Results obtained were indicated in a maximum dilution ratio at which absorbance is doubled or more than the absorbance of IgY prior to immunization.

Table 1 shows the results of reactivity (ELISA) of ostrich yolk antibodies obtained by immunizing with a homogenate solution of *S. aureus* cells. Each numerical value is in a maximum dilution ratio at which absorbance is doubled or more than the absorbance of IgY obtained from a yolk of an ostrich prior to immunization. Thus, the unit of the values is "times". For example, for enterotoxins, it means that even when diluted 12,800 times in comparison to an ostrich yolk antibody without immunization with a homogenate solution, the absorbance value was double or greater. This indicates that an antibody with a high titer to such an extent is obtained.

TABLE 1

| *S. aureus* cell | enterotoxin | TSST-1 | coagulase | protease |
|---|---|---|---|---|
| 6,400 | 12,800 | 51,200 | 51,200 | 102,400 |

An antibody with a high titer against not only microbial cells but also enterotoxins, super antigen TSST-1, coagulase, and protease was produced by immunizing an ostrich with a homogenate solution of a *S. aureus* cell. Enterotoxins, super antigen TSST-1, coagulase, and protease are factors that progress the deterioration of a lesion from *S. aureus* cells, and it was possible to readily obtain antibodies against them by simply inoculating microbial cells.

Table 2 shows the result of ELISA for an ostrich yolk antibody obtained by immunizing an ostrich with a homogenate solution of *P. acnes* cells. Similar to the above, the numerical value is in a maximum dilution ratio at which absorbance is doubled or more than the absorbance of IgY prior to immunization. Thus, the unit of the value is "times". A result has not been obtained for factors that progress a lesion, such as enterotoxins. However, a high titer was exhibited for *P. acnes* cells.

TABLE 2

| *P. acnes* cell | enterotoxin | TSST-1 | coagulase | protease |
|---|---|---|---|---|
| 12,800 | — | — | — | — |

Bacterial Proliferation Inhibiting Effect of Ostrich Yolk Antibody (Assessment by PFU)

Ostrich yolk antibodies were mixed with a bacterial solution (*S. aureus* or *P. acnes*) prior to culturing so that the concentration is 1 mg/mL, and each mixture was cultured for 18 hours in an agar medium (0.1 ml of bacterial solution was cultured in a Petri dish with a radius of 10 cm). Bacterial colonies were counted to calculate PFU (plaque-forming unit). The results thereof are shown in FIG. 1. FIG. 1(*a*) is for *S. aureus*, and FIG. 1(*b*) is for *P acnes*. The horizontal axis indicates a case of an antibody prior to immunization and a case of an antibody after immunization. The vertical axis is the PFU ($\times 10^5/100$ μL). Both antibodies inhibited proliferation of bacteria, which is the antigen.

Bacterial Proliferation Inhibiting Effect of Ostrich Yolk Antibody (Assessment by Agar Medium)

Ostrich yolk antibodies (antibodies obtained by immunizing with *S. aureus*) were mixed with a solution of *S. aureus* prior to culturing so that the concentration becomes 1 mg/mL, and the mixture was cultured for 18 hours in an agar medium (0.1 ml of bacterial solution was cultured in a Petri dish with a radius of 10 cm). The results are shown in the pictures of FIG. 2, which are results of mixing antibodies prior to immunization (FIG. 2(*a*) left picture) and after immunization (FIG. 2(*b*) right picture). It can be understood that the number of colonies of bacteria (white dots) was clearly decreased by mixing with immune antibodies, i.e., proliferation of bacteria was inhibited by antibodies.

Effect of Ostrich Antibody on Atopy and Acne

An ostrich yolk antibody made by immunization with *S. aureus* or *P. acnes* was mixed with petrolatum (base) (antibody concentration was adjusted to be 50 μg/mL), and the mixture was applied as an ointment to subjects suffering from atopy or acne on infected area. The mixture was continuously used twice daily, and condition of the infected area was observed after one week. Only the base was used on control subjects. The results are shown in Table 3. In this Table, "*S. aureus* antibodies" indicate antibodies obtained by using a homogenate solution of *S. aureus* cells as an antigen, and "*P. acnes* antibodies" indicate antibodies obtained by using a homogenate solution of *P. acnes* cells as an antigen. In addition, "Mixed antibodies" refer to "*S. aureus* antibodies" and "*P. acnes* antibodies" mixed at a 50:50 ratio, which is mixed with a base (concentration of the entire antibodies is adjusted to be 50 μg/mL).

TABLE 3

| Name of antibody | Alleviation in atopic symptom | Alleviation in acne symptom |
|---|---|---|
| *S. aureus* antibodies | 73% (49/67) | 13% (5/39) |
| *P. acnes* antibodies | 17% (11/65) | 69% (34/49) |
| Mixed antibodies | 81% (50/76) | 59% (30/51) |
| Base only | 16% (12/76) | — |

An antibody containing ointment alleviated a symptom. Further, an ointment in which two types of antibodies were mixed had an effect on both atopy and acne. The numbers in parentheses indicate the number of cases where alleviation in a symptom was confirmed among the number of cases. For example, (49/67) indicates that alleviation in a symptom was observed in 49 out of 67 cases. This is 73% when converted into percentages.

EXAMPLE 2

Since a virus enters a cell after infection, it is difficult to inhibit the proliferation or development thereof with an antibody. However, it is expected that a viral infection itself can be inhibited by having an antibody bind to the surface of a virus to change the surface condition prior to infection. Especially, a viral infection often occurs by mucous membranes contacting each other. Thus, it is expected that infections can be dramatically inhibited by applying in advance an antibody against a mucous membrane at the time of such an act.

The summary of experiments is as follows. AIDS virus and papilloma virus were used as Examples. An AIDS virus is a virus capsulated in a spherical envelope, and the surface thereof has proteins gp120 and gp41. Further, a papilloma virus is a cyclic double-stranded virus and is a non-enveloped type virus. In addition, it has an L1 protein in a part thereof.

For AIDS virus, gp120 and a precursor thereof, gp160, were used as an antibody. For papilloma virus, L1 was used. Since cell culturing is not easy for viruses, such proteins were produced as a recombinant protein with genetic engineering by a baculovirus.

In addition, a female ostrich was immunized with the produced protein as an antigen to obtain an egg laid by the ostrich. An antibody was then purified from the egg and the titer thereof was examined by ELISA. A detailed description is provided below.

Human Immunodeficiency Virus (Hereinafter, Referred to as "HIV") Antigen

Instead of HIV itself, surface proteins of HIV, recombinant proteins HIV gp120 and HIV 160 produced with genetic engineering by baculovirus, were used as an antigen. HIV gp120 and HIV gp160 are proteins needed for HIV to infect human cells. Thus, it is conceived that an HIV infection can be inhibited if antibodies against such proteins are produced. A mixture of 50 μg of HIV gp120 and 50 μg of HIV gp160 was used for immunization of an ostrich.

Human Papilloma Virus (Hereinafter, Referred to as "HPV") Antigen

HPV types 6, 11, 16, and 18 that induce cervical cancer were used (total of four types of antigens). Instead of HPV itself, an L1 protein (recombinant protein) of the virus produced with genetic engineering by a baculovirus was used as an antigen. A mixture of the above-described four types of antigens (40 μg each) was used for immunization of an ostrich.

Recombinant proteins were produced in accordance with a conventional method. Specifically, a viral cDNA was used to amplify only the L1 protein region by PCR, and the product thereof was introduced into a baculovirus vector. The vector was then introduced into Sf9 cells, and a recombinant protein was purified from the culture solution and cell extract thereof.

Immunization of Ostrich

Each of HIV and HPV was used for immunization of separate ostriches. 100 μg, in terms of protein abundance, of the viral antigen described above was mixed with a Freund's complete adjuvant and the mixture was inoculated in the muscle at the lumbar region of a female ostrich as a prime immunization. Further, the two viruses described above were both administered three times every other week as a booster immunization after the prime immunization. 100 μg of antigen was mixed with a Freund's incomplete adjuvant, and the mixture was inoculated into the muscle at the lumbar region of the female ostrich.

Purification of Antibody

An antibody was purified from an ostrich egg laid two weeks or more after the booster immunization. A method of purifying the antibody is shown below.

Purification of an antibody (IgY) from a yolk was performed as follows. First, TBS (Tris-Buffered Saline: 20 mM Tris-HCl, 0.15 M NaCl, and 0.5% NaN$_3$) at five times the amount of a yolk and the same amount of 10% dextran sulfate/TBS are added to the yolk, and the mixture is stirred for 20 minutes. In addition, the same amount of 1M CaCl$_2$/TBS is added, and the mixture is stirred and is incubated for 12 hours. Thereafter, the mixture is centrifuged at 15000 rpm for 20 minutes, and the supernatant is collected.

Next, ammonium sulfate is added so that the final concentration becomes 40%, and the mixture is incubated at 4° C. for 12 hours. Thereafter, the mixture is centrifuged at 15000 rpm for 20 minutes and precipitates are collected. Finally, it is resuspended in the same amount of TBS as the yolk, and dialyzed with TBS. Collection of IgY with a purity of 90% or more was enabled by such a process. 2-4 g of IgY was able to be purified from one yolk.

Measurement by ELISA

Antibody reactivity of an obtained antibody was measured by the following ELISA. 100 µl of each of 2 µg/mL HIV gp120, HIV gp160, HPV type 6, 11, 16, and 18 was placed in each well of a 96-well microplate for ELISA and was incubated at room temperature for two hours.

After washing three times with PBS (Phosphate buffered saline), 100 µg of a commercially available blocking solution (Block Ace: Dainippon Sumitomo Pharma Co., Ltd.) was placed in each well and the mixture was incubated for two hours. After washing three times with PBS, 50 µg of a serial dilution solution (with 2 mg/mL as the stock solution, a two-fold serial dilution was continuously performed, e.g., 100 times, 200 times) of an ostrich IgY antibody prior to and after immunization was placed in each well and the mixture was incubated for one hour.

After washing three times with PBS, 100 µg of peroxidase labeled anti-ostrich IgY rabbit polyclonal antibody (self-produced) was placed in each well and the mixture was incubated for 45 minutes. After washing three times with PBS, a commercially available luminescence kit for peroxidase (Sumitomo Bakelite Co., Ltd) was used and 30 minutes after the emission of luminescence, the absorbance (450 nm) was measured by a plate reader for ELISA. Results obtained were indicated in a maximum dilution ratio at which absorbance is doubled or more than the absorbance of IgY prior to immunization.

Mixture into Lotion

The ostrich yolk antibodies described above (HIV, HPV) were mixed into a lotion (used directly upon intercourse, or also used on condom surface). 1 mg of ostrich yolk antibody was mixed with 10 mL of lotion (components: water, glycerol, ethanol, sodium polyacrylate, hydroxyethyl cellulose, phenoxyethanol, EDTA-2Na, paraben, polysorbate 80, fatty acid sorbitan). Antibody activity (each of the antigens HIV and HPV) in the mixed solution was similarly measured by ELISA as described above.

Results

Table 4 shows the results of ELISA for cases of HIV gp120 and HIV gp160. The values in the Table are the maximum dilution ratio at which absorbance is doubled or more than the absorbance value of antibodies prior to immunization. It was found that antibodies with a high titer against HIV gp120 and HIV gp160, which are important factors in an HIV infection, were produced. Further, it was found that there is no loss in antibody activity even when mixed into a lotion.

TABLE 4

| | antibody titer of ostrich yolk antibody (ELISA) (maximum dilution rate at which absorbance is double or more than the absorbance of antibodies prior to immunization) | |
|---|---|---|
| | HIVgp120 | HIVgp160 |
| yolk antibody from ostrich immunized with mixed solution of HIV gb120 or HIV gb160 (stock solution: 1 mg/10 mL PBS) | 102,400 | 51,200 |
| lotion mixture (1 mg/10 mL) | 102,400 | 51,200 |

Table 5 shows results of ELISA for HPV. Similar to Table 4, the values in the Table are the maximum dilution ratio at which absorbance is doubled or more than the absorbance of antibodies prior to immunization. HPV types 6, 11, 16, and 18 induce human cervical cancer. In ostriches, it was found that antibodies with a high titer against L1 protein (protein important for infection) of such viruses are produced. Further, high reactivity was exhibited against each HPV antigen even when mixed into a lotion.

TABLE 5

| | antibody titer of ostrich yolk antibody against HIP L1 protein (ELISA) (maximum dilution rate at which absorbance is double or more than the absorbance of antibodies prior to immunization) | | | |
|---|---|---|---|---|
| | HPV type 6 | HPV type 11 | HPV type 16 | HPV type 18 |
| yolk antibody from ostrich immunized with mixed solution of HPV types 6, 11, 16, and 18 (stock solution: 1 mg/ 10 mL PBS) | 102,400 | 204,800 | 102,400 | 102,400 |
| lotion mixture (1 mg/10 mL) | 51,200 | 51,200 | 102,400 | 51,200 |

INDUSTRIAL APPLICABILITY

An antibody of the present invention can be applied to other skin indigenous bacteria such as *micrococcus* or *Tricophyton*, which is a pathogenic microbe causing tinea pedis, to inhibit or treat an infection by pathogens infected through mating (infection by contact), such as HIV, *Chlamydia*, and herpesvirus, as well as to a palliative or a therapeutic agent (ointment, nasal drop, eye drop) for allergies caused by pollen (cedar, cypress, ragweed).

Further, an antibody of the present invention can be widely used as an infection inhibitor against not only AIDS virus and papilloma virus, but also viruses with a known surface protein.

The invention claimed is:

1. A lotion, comprising:
    ostrich antibodies which specifically bind to a surface protein of a virus, wherein the virus comprises any one of HPV type 6, 11, 16 or 18; and
    water, glycerol, ethanol, sodium polyacrylate, hydroxyethyl cellulose, phenoxyethanol, EDTA-2Na, paraben, polysorbate 80, and fatty acid sorbitan.
2. The lotion of claim 1, wherein the antibodies are IgY antibodies obtained from an egg of an ostrich immunized with the surface protein as an antigen.

3. The lotion of claim 2, wherein the virus comprises HPV type 6,11, 16 and 18.

4. The lotion of claim 3, wherein the surface protein comprises an HPV L1 protein.

5. The lotion of claim 1, for use in preventing or treating virus infection.

* * * * *